(12) United States Patent
Fleischer (10) Patent No.: US 9,427,276 B2
(45) Date of Patent: Aug. 30, 2016

(54) METHOD OF CHANGING POSITION OF BONES

(71) Applicant: Gary D Fleischer, Kensington, NH (US)

(72) Inventor: Gary D Fleischer, Kensington, NH (US)

(*) Notice: Subject to any disclaimer, the term of this patent is extended or adjusted under 35 U.S.C. 154(b) by 0 days.

(21) Appl. No.: 14/488,706

(22) Filed: Sep. 17, 2014

(65) Prior Publication Data

US 2015/0080956 A1   Mar. 19, 2015

Related U.S. Application Data

(60) Provisional application No. 61/878,731, filed on Sep. 17, 2013, provisional application No. 61/878,734, filed on Sep. 17, 2013.

(51) Int. Cl.
| | |
|---|---|
| *A61F 2/44* | (2006.01) |
| *A61B 17/88* | (2006.01) |
| *A61F 2/46* | (2006.01) |
| *A61B 17/70* | (2006.01) |

(52) U.S. Cl.
CPC ....... *A61B 17/8866* (2013.01); *A61B 17/7041* (2013.01); *A61F 2/4455* (2013.01); *A61F 2/4611* (2013.01)

(58) Field of Classification Search
CPC .... A61F 2/4455; A61F 2/446; A61F 2/4465; A61F 2/447; A61F 2/4611
See application file for complete search history.

(56) References Cited

U.S. PATENT DOCUMENTS

| | | | |
|---|---|---|---|
| 6,375,683 B1 * | 4/2002 | Crozet | B65D 5/48022 623/17.15 |
| 2002/0010511 A1 * | 1/2002 | Michelson | A61F 2/4455 623/17.15 |
| 2004/0254574 A1 | 12/2004 | Morrison | |
| 2005/0187548 A1 | 8/2005 | Butler | |

FOREIGN PATENT DOCUMENTS

DE          3415294 A1    10/1985

OTHER PUBLICATIONS

Notification of Transmittal of the International Search Report and Written Opinion of the International Searching Authority(PCT/US2014/056124) dated Feb. 23, 2015—12 pages.

* cited by examiner

*Primary Examiner* — Eduardo C Robert
*Assistant Examiner* — Julianna N Harvey
(74) *Attorney, Agent, or Firm* — Michael A. Bondi; Moss & Barnett (57) ABSTRACT

A pedicle screw system that includes a pedicle screw and a collar. The pedicle screw includes an insertion portion, a shaft portion that extends from the insertion portion, and a head portion that is attached to the shaft portion. The head portion has a diameter that is larger than the shaft portion. The collar includes a first aperture and a second aperture. The first aperture and the second aperture are both adapted to receive the head portion. The first aperture includes a first aperture section and a second aperture section. The first aperture section is larger than the head portion. The second aperture section is smaller than the head portion.

13 Claims, 6 Drawing Sheets

METHOD OF CHANGING POSITION OF BONES

REFERENCE TO RELATED APPLICATION

This application claims priority to U.S. Application Nos. 61/878,731 and 61/878,734, which were both filed on Sep. 17, 2013, the contents of which are hereby incorporated by reference.

FIELD OF THE INVENTION

The invention relates generally to orthopedic devices. More particularly, the invention relates to a pedicle screw system.

BACKGROUND OF THE INVENTION

Pedicle screw systems have been in common practice for fusion procedures of the spine for several decades. The screw systems are placed using a posterior approach, either open or minimally invasive, in all areas of the spine from C1 to the sacrum.

The pedicle screw systems are typically deployed bi-laterally but can be used unilaterally. The purpose of the pedicle screw systems is to immobilize one or more motion segments, adjacent vertebral bodies and inter-vertebral disc. The immobilization is typically done as part of a fusion procedure.

These immobilizing constructs can bridge as few as one motion segment as would be typical for a one level fusion or many levels as would be typical for treating conditions such as scoliosis.

A typical pedicle screw system consists of a long bone screw that is placed through the pedicle and into the vertebral body on one or both sides of a vertebral body. This screw is typically terminated proximally with a mechanism for capturing and holding a rod that runs longitudinally between all of the pedicle screws employed, one rod on each side of the vertebral body.

The rods are typically manufactured with a straight configuration. Either during or prior to the surgical procedure, the rods are formed by the surgeon into a three dimensionally "bent" rod that will conform, as best as can be approximated, to the curvature and angulation of the spine. The rods are generally inserted into a "U" shaped receiver at the terminal end of the pedicle screw, the receiver having the ability to swivel, pivot and rotate, i.e., "polyaxial" so as to accept and capture the formed rod.

A set-type screw is threaded into the proximal end of the U receiver and tightened against the rod, thus holding it in place. Once fully in place, the pedicle screw construct will immobilize the treated motion segment(s) thereby creating a proper environment for the treated motion segments to fuse.

Currently, pedicle screw systems tend to be fairly bulky with a significant amount of screw and locking mechanism protruding beyond the vertebral body. This protrusion can irritate muscle tissue and may prove to be an annoyance to the patient. Implantation of the screws can be difficult for the surgeon as positioning each screw and the longitudinal rod(s) involves a great deal of steps.

Perhaps most critical is the degree of mechanical compromise inherent in traditional pedicle screw constructs. The "open" configuration is a compromise, mechanically, to accommodate in situ preparation and assembly of the pedicle screw construct. When compared to an "ideal" closed system wherein the rod is completely encircled and captured into the terminal end of the pedicle screw is inherently weaker and less rigid. Fully closed systems are not practical however, as anatomical access, variability from patient to patient and unique hand work of surgery prevent their application.

SUMMARY OF THE INVENTION

An embodiment of the invention is directed to pedicle screw system that includes a pedicle screw and a collar. The pedicle screw includes an insertion portion, a shaft portion that extends from the insertion portion, and a head portion that is attached to the shaft portion. The head portion has a diameter that is larger than the shaft portion.

The collar includes a first aperture and a second aperture. The first aperture and the second aperture are both adapted to receive the head portion. The first aperture includes a first aperture section and a second aperture section. The first aperture section is larger than the head portion. The second aperture section is smaller than the head portion.

Another embodiment of the invention is direct to a pedicle screw system that includes a pedicle screw, a collar, an elongated rod and a screw. The pedicle screw includes a shaft portion and a head portion that is attached to the shaft portion. The head portion has a diameter that is larger than the shaft portion.

The collar includes a first aperture and a second aperture. A recess is defined between the first aperture and the second aperture. The first aperture and the second aperture are both adapted to receive the head portion. The first aperture includes a first aperture section and a second aperture section. The first aperture section is larger than the head portion. The second aperture section is smaller than the head portion. The elongated rod is positionable in the recess. The screw is capable of engaging the collar and the elongated rod to retain the elongated rod in a position with respect to the collar.

Another embodiment of the invention is directed to a method of operating a pedicle screw system. A collar is provided that includes a first aperture and a second aperture. A recess is defined between the first aperture and the second aperture. The first aperture includes a first aperture section and a second aperture section.

A pedicle screw is provided that includes a shaft portion and a head portion that is attached to the shaft portion. The head portion has a diameter that is larger than the shaft portion. The first aperture section is larger than the head portion. The second aperture section is smaller than the head portion. A portion of an elongated rod is positioned in the recess. The head portion is extended through the first aperture and the second aperture. The shaft portion is positioned at least partially in the second aperture section to retain the collar on the pedicle screw and the elongated shaft in the recess.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

The invention is directed to a pedicle screw system as illustrated in the figures submitted herewith. In certain embodiments, the pedicle screw system 10 includes a pedicle screw 12 and a collar 14, as illustrated in the drawings. The pedicle screw 12 and the collar 14 are selectively attachable for use in conjunction with a surgical procedure such as a spinal fusion where vertebrae are maintained in a substantially stationary position with respect to each other.

The benefits of this pedicle screw system 10 are the relative ease of application inherent in a top loading pedicle screw system plus the mechanical rigidity of a functionally closed system. The collar 14 will accommodate variability in multi-axial orientation, thus affecting a polyaxial system.

In addition, the pedicle screw system 10 will offer a lower profile construct and enhanced management during surgery as the longitudinal rod is better captured and more easily positioned and held. It is envisioned that the time of surgery will also be significantly reduced as positioning and control will be simplified.

The pedicle screw 12 has an insertion portion 20 that is capable of being inserted into a bone. While it is illustrated that the insertion portion 20 has a tapered configuration, it is possible for the insertion portion 20 to have a variety of configurations using the concepts of the invention. For example, at least a part of the insertion portion 20 may have a cylindrical shape.

Threads extend over at least a part of a surface of the insertion portion 20. The threads may have a variety of thread pitches and/or depths using the concepts of the invention. The thread depth and/or pitch may be selected based upon factors such as the bone in which the pedicle screw 12 is intended to be used. In certain embodiments, the thread pitch and/or depth varies at different locations on the insertion portion 20.

While increasing a length of the insertion portion 20 increases the potential of the pedicle screw 12 to reduce movement after insertion into a bone, the length of the insertion portion 20 may be selected based upon the intended use of the pedicle screw system 10 such as the depth of the bone in which it is intended to insert the insertion portion 20.

A diameter of the insertion portion 20 may be selected based upon the material from which the pedicle screw 12 is fabricated to provide the insertion portion 20 with sufficient strength to withstand bending and/or breaking during the insertion process as well as after implantation in a patient. However, the diameter should be as small as possible to minimize the size of the aperture that needs to be formed in the bone.

In still other embodiments, the insertion portion 20 may be formed without threads. In such embodiments, the surface of the threaded portion 20 may be treated and/or covered with at least one material that causes the insertion portion 20 to resist moving after being inserted into an aperture formed in a bone. The insertion portion 20 may also be coated with a material that fosters bone growth.

The pedicle screw 10 also includes a shaft portion 22 that extends from the insertion portion 20. In certain embodiments, the shaft portion 22 may have a generally cylindrical configuration. A person of skill in the art will appreciate that the shaft portion 22 may have a variety of other configurations, examples of which include triangular, square and hexagonal.

As illustrated in the figures, the shaft portion 22 may have a diameter that is less than a diameter of the insertion portion 20. In other embodiments, the shaft portion 22 may have a diameter that is the same as or less than the diameter of the insertion portion 20. In situations where the diameter of the shaft portion 22 is not less than the diameter of the insertion portion 20, a stop mechanism (not shown) may be provided to restrict the ability of the collar 14 to move over the insertion portion 20.

A length of the shaft portion 22 may be selected based upon the intended use of the pedicle screw system 10 such as the dimensions of the rod 40 that is to be used in conjunction with the pedicle screw system 10. In certain embodiments, it is desired for the shaft portion 22 to be as short as possible to minimize a distance that the pedicle screw 12 extends from the vertebra.

A diameter of the shaft portion 22 may be selected based upon the material from which the pedicle screw 12 is fabricated to provide the shaft portion 22 with sufficient strength to withstand bending and/or breaking after implantation in a patient. However, the diameter should be as small as possible to minimize the size of the other components that are used in conjunction with the pedicle screw 12 such as the collar 14.

While the shaft portion 22 is illustrated as being substantially cylindrical, it is possible for the shaft portion to have a concave shape to increase the surface area over which the shaft 40 contacts the shaft portion 22 to thereby reduce the potential of the shaft moving with respect to the pedicle screw 12. In another embodiment, the shaft portion 22 includes a V-shape. Such a configuration also increases the surface area over which the shaft 40 contacts the pedicle screw 12.

An end of the shaft portion 22 that is opposite that insertion portion 20 includes a head 24 that is used in conjunction with removably attaching the pedicle screw 12 to the collar 14. Accordingly, the head 24 should have at least one dimension that is larger than the shaft portion 22.

The size of the head 24 should be sufficiently large to minimize the potential of the collar 14 inadvertently disengaging from the shaft portion 22 as is discussed in more detail below. While it is illustrated that the head 24 has a generally circular configuration, it is possible for the head 24 to have a variety of shapes, examples of which include oval, triangular and square.

The collar 14 may be formed with an elongated configuration. In certain embodiments, the collar 14 may be formed in a U-shape that includes two collar legs 30 and a recess 32 that is defined between the collar legs 30. The length and width of the collar legs 30 can be selected based upon a variety of factors such as the diameter of the rod 40.

At least a portion of the collar 14 may be fabricated from a flexible material to facilitate bending the collar 14 when the collar 14 is attached to and detached from the pedicle screw 12. In certain embodiments, at least a portion of the collar 14 is fabricated from a resilient material that is capable of bending from a generally linear configuration upon application of a force and then returning to the initial configuration when the force is discontinued.

The collar 14 may be configured with a variable cross-section where a generally central section may be thicker than the ends where the shaft apertures 34 are placed. The thicker central section provides enough thickness for an aperture to be drilled and tapped to accept a tightening screw, as discussed in more detail below.

It is also possible for the collar 14 to be fabricated from thinner material proximate opposite ends thereof. Using such a configuration increases the flexibility of the collar legs 30.

Proximate an end of each of the collar legs 30, a shaft aperture 34 is formed therein. The shaft aperture 34 includes a first aperture section 36 and a second aperture section 38 that intersect each other. In certain embodiments, the second aperture section 38 may be located closer to the end of the collar leg 30 than the first aperture section 36.

The shape and size of the first aperture section 36 may be selected based upon the shape and size of the head 24 so that when the collar 14 is being moved into engagement with the pedicle screw 12, it is possible for the head 24 to pass through the first aperture section 36. In certain embodiments, the first aperture section 36 may have a partially circular configuration with a diameter that is slightly larger than a diameter of the head 24. If the head 24 has a non-circular shape, it may be necessary for the head 24 to be positioned in a particular orientation for the head 24 to pass through the first aperture section 36.

The shape and size of the second aperture section 38 may be selected based upon the shape and size of the shaft portion 22 and the head 24. The second aperture section 38 may have a width that is smaller than a width of the head 24. The second aperture section 38 may have a width that is greater than a width of the shaft portion 22. Using such a configuration enables the shaft portion 22 to be retained on the collar 14 once the shaft portion 22 is moved into the second aperture section 38. In certain embodiments, the second aperture section 38 may have a partially circular configuration.

At least a portion of the surface of the second aperture section 38 may have a surface texture and/or coating that increases friction between the shaft portion 22 and the second aperture section 38 to thereby limit movement of the collar 14 with respect to the pedicle screw 12 after the collar 14 is attached to the pedicle screw 12.

Additionally or alternatively, the shaft portion 22 may have a surface texture and/or coating that also increase friction between the shaft portion 22 and the second aperture section 38 to limit movement of the collar 14 with respect to the pedicle screw after the collar 14 is attached to the pedicle screw 12.

The shaft aperture 34 formed in each of the collar legs 30 may be substantially similar. Using such a configuration enables the collar 14 to be attached to the pedicle screw 12 with either of the collar legs 30 oriented towards the pedicle screw 12. In an alternative embodiment, the shaft aperture 34 on the lower collar leg 30 may be formed without the second aperture section 38. The only important criterion in such a configuration is that the shaft aperture 34 be sufficiently large so that the head 24 can pass therethrough.

In certain embodiments, it may be desired to limit movement of the pedicle screw 12, collar 14 and the shaft 40 with respect to each other. In such situations, a screw aperture 44 may be formed at an intermediate location on the collar 14. The screw aperture 44 may be tapped so that a screw 42 can engage the collar 14 through the screw aperture 44.

Figure 6:
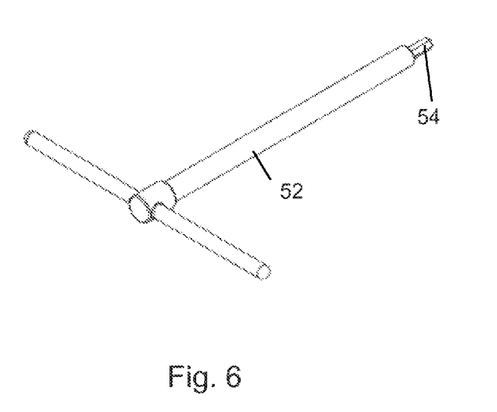
FIG. 6 is a tool for use in conjunction with the pedicle screw system.

The head 24 includes a mechanism that enhances the ability to rotate the pedicle screw 12. In certain embodiments, the mechanism is a recess 46 formed in the head 24. The recess 46 may include a variety of shapes such as square and hexagonal. A tool 52 (FIG. 6) may have a tip 54 with a shape that is complementary to the recess 46 such that at least a portion of the tip 54 may be inserted in the recess 44 to facilitate rotating of the pedicle screw 12.

As the screw 42 is tightened, a distal end thereof contacts the rod 40 to urge the rod 40 towards the shaft portion 22. Progressive tightening of the screw 42 thereby restricts movement of the pedicle screw 12, the collar 14 and the rod 40 with respect to each other. This process also causes the shaft portion 22 to move more deeply into the second aperture section 38, which reduces the potential of the collar 14 being detached from the pedicle screw 12.

It is also possible to use multiple screws. One screw 42 can be used per pedicle in one or both lateral sides of the selected vertebral bodies with the screws on each side of the spine being connected to the longitudinal rod(s).

Figure 7:
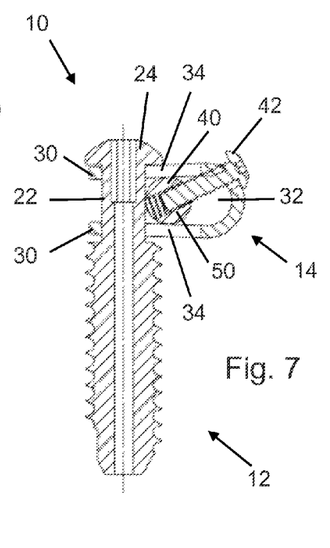
FIG. 7 is a sectional view of an alternate configuration of the pedicle screw system.

In an alternative embodiment, the shaft 40 includes an aperture 50 that is adapted to receive at least a portion of the screw 42, as illustrated in FIG. 7. This configuration enables the screw 42 to engage the pedicle screw 12 and thereby further reduce the potential of the pedicle screw 12 moving with respect to the collar 14.

In yet another embodiment, the screw 42 may be oriented at an angle with respect to the shaft 40 so that the tip of the screw 42 does not contact the shaft 40. Such a configuration could be viewed as a glancing blow and increase the ability of the screw 42 to retain the shaft 40 in a stationary position with respect to the pedicle screw 12.

Figure 8:
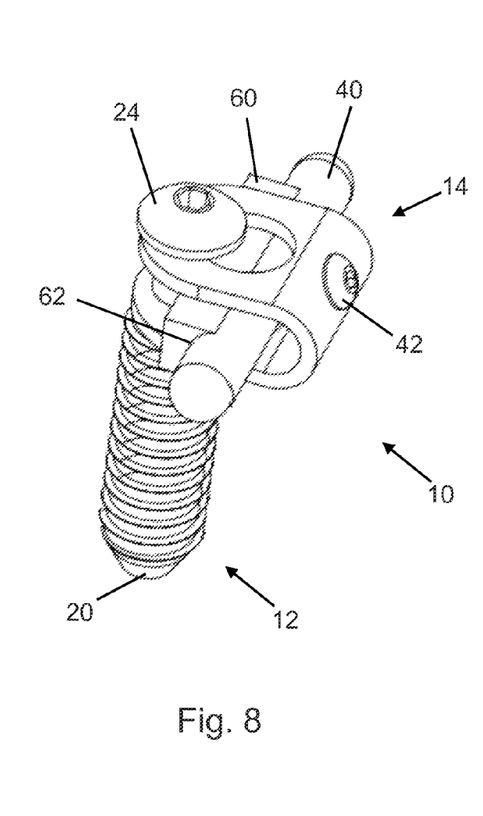
FIG. 8 is a perspective view of a pedicle screw system according to an alternative embodiment of the invention where the pedicle screw system is in an assembled configuration.
Figure 9:
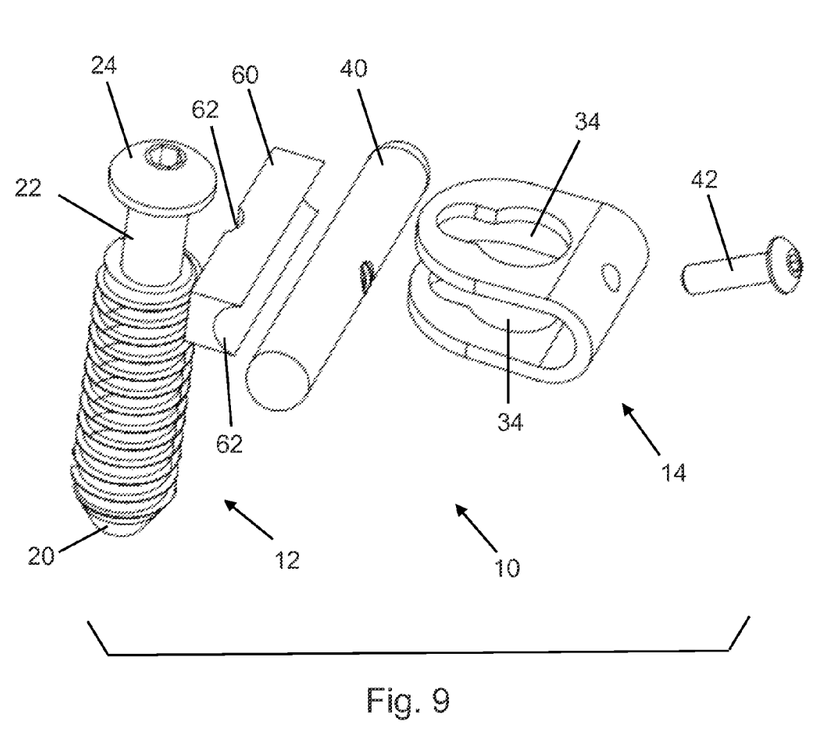
FIG. 9 is a perspective view of the pedicle screw system of FIG. 8 in an exploded configuration.

To further increase the surface area over which the shaft 40 engages the pedicle screw 12, it is possible to use a spacer 60 that is positioned between the shaft 40 and the pedicle screw 12, as illustrated in FIGS. 8 and 9. The spacer 60 may include concave and/or V-shaped surface 62 to increase the surface area over which the shaft 40 engages the spacer and the pedicle screw 12 engages the spacer 60. At least one of the engagement surfaces may be coated with a material that increases the friction with the shaft 40 and/or the pedicle screw 12.

In operation, an aperture is formed in a bone where it is intended to attach the pedicle screw 12. The aperture may have a shape that at least partially conforms to a shape of the insertion portion 20. The insertion portion 20 is then extended into the aperture until the pedicle screw 12 is in engagement with the aperture such that the pedicle screw 12 resists movement with respect to the bone.

The collar legs 30 are urged towards each other and the head 24 is extended through the first aperture section 36 on both of the collar legs 30. When the force on the collar legs 30 is removed, the resilient nature of the collar 14 causes the collar legs 30 to move apart from each other until one of the collar legs 30 contacts the head 24 and the other collar legs 30 contacts the wider insertion portion 20. This process may also cause the shaft portion 22 to move from the first aperture section 36 to the second aperture section 38 to thereby retain the collar 14 on the pedicle screw 12. The rod 40 may be placed in the recess 32 either before or after the collar 14 is attached to the pedicle screw 12.

The screw 42 is then rotated with respect to the collar 14, which causes the end of the screw 42 to contact the rod 40 and urge the rod toward the shaft portion 22. The process is continued until the pedicle screw 12, the collar 14 and the rod are in a substantially stationary position with respect to each other. This force also causes the shaft portion 22 to move more deeply into the second aperture section 38, which limits pivoting of the collar 14 with respect to the pedicle screw 12.

Another embodiment of the invention is directed to an orthopedic implant system. This invention contemplates a system of implantable devices that will establish and maintain a desired relative position between adjacent structures in a body. This invention also anticipates and describes instruments or tools configured to apply rotational force, known as drivers and other instrumentation for use by the surgeon when using the system in surgery.

The implantable devices are configured to provide biomechanically preferred positioning of adjacent structures in the body for the purpose of creating and maintaining a minimum fixed distance between two structures such as bone and more specifically adjacent vertebrae in a spine, i.e., inter-body implants capable of separating or distracting adjacent vertebrae in the spine where one or more rotationally adjustable, generally cylindrical devices with cross-sectional geometry that may be round, oval or cam shaped, either symmetrical or asymmetrical may be employed.

The present invention differs from other inter-body spacers described in the art in that the distracting action of the cam-shaped cylinders acts directly against the bones without an intermediate end-plate and the relative contact area of cam shaped cylinder with the bones is significantly less than the contact area of a typical implant end-plate this allowing significantly more area for bone growth between the adjacent bones.

Additionally, as each cam-shaped cylinder is deployed, adjusted and acts independently, the relative position of the adjacent bones can be established at an anatomically and biomechanically advantageous angle as determined by the surgeon.

Multiple, independently deployable and adjustable devices may be incorporated in any given surgery to create a final relationship between adjacent structures that may be parallel or non-parallel with respect to each other in a configuration determined by the surgeon at the time of surgery. Additional implantable apparatus may be employed to maintain the relative position of the cylindrical devices so as to maintain their relative position and that of the bone-implantable device assembly construct.

The additional apparatus may include holders and locking mechanisms to form a biomechanical structure establishing and maintaining the geometrical space between two adjacent bone surfaces or vertebral bodies. The implant system may include cylindrical implants of varying cross-sectional geometries, instruments to insert and manipulate the cylinders into their desired position and alignment, and integrated accommodations on the cylinders to attach into holders that will remain as implants and help to distribute the forces between the cylindrical spacers and the bone and or as a locking mechanism to maintain the relationship between multiple cylinder and to lock their rotations. The holder may or may not also provide places for fixation of the assembled device components to the adjacent bones.

In certain embodiments, this invention contemplates the use of at least one cam-shaped cylinder placed in a space between the adjacent bones or vertebral bodies. The cam-shaped cylinder can then be rotated to dynamically adjust the space between the adjacent bone surfaces or vertebral body endplates and would remain in place as an implant to maintain the desired relationship between the adjacent bone surfaces.

Figure 10:
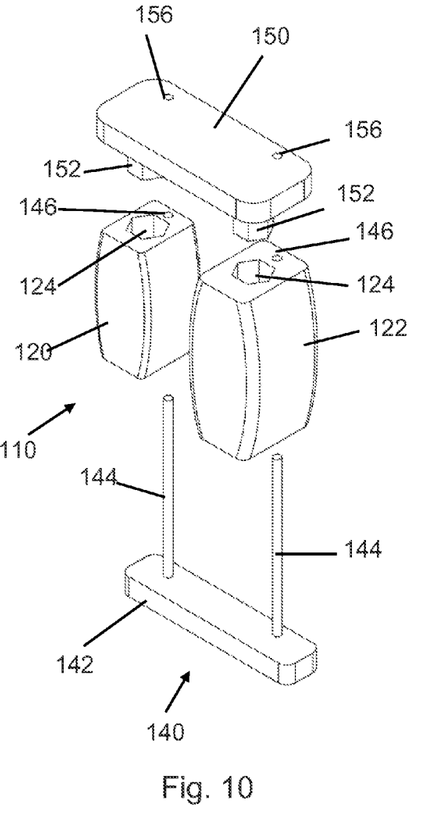
FIG. 10 is a perspective view of an orthopedic implant system according to an embodiment of the invention wherein the orthopedic implant system is in an exploded configuration.
Figure 11:
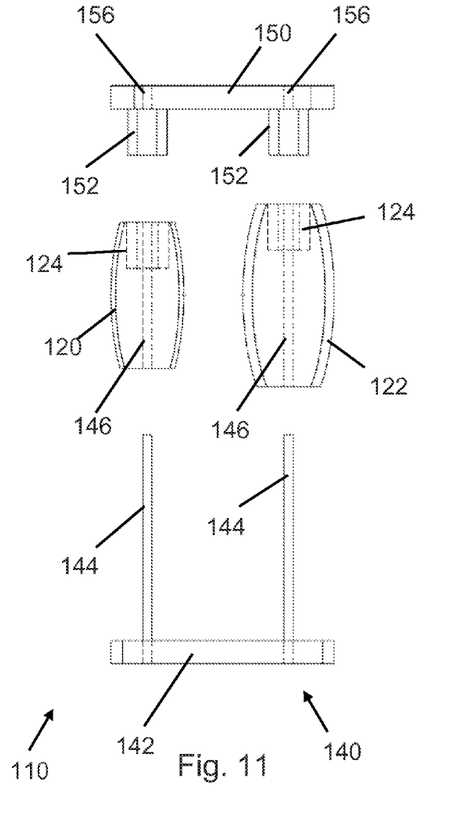
FIG. 11 is a side view of the orthopedic implant system of FIG. 10.
Figure 12:
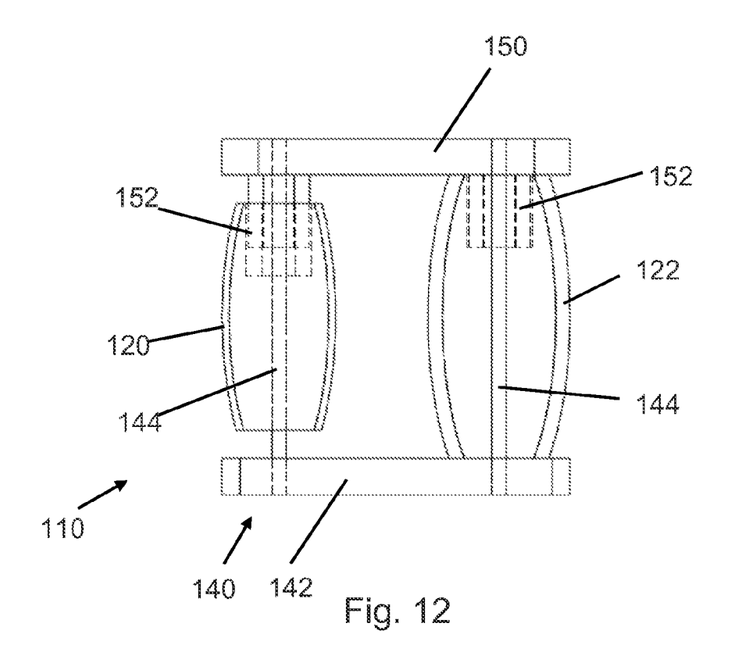
FIG. 12 is a side view of the orthopedic implant system in an engaged configuration.

An embodiment of the orthopedic implant system is illustrated at 110 in FIGS. 10-12. The orthopedic implant system 110 includes a first cam body 120 and a second cam body 122. In certain embodiments, the first and second cam body 120, 122 each have a similar configuration. In other embodiments, the first and second cam body 120, 122 have different configurations.

At least a portion of one of the first and second cam body 120, 122 may have a non-cylindrical profile such that as the first and/or second cam body 120, 122 are rotated, the first and/or second cam body 120, 122 causes distraction of tissue positioned on opposite sides thereof.

The first and second cam body 120, 122 may have varying geometries with variable diameters and cross-section geometries, allowing variable radii of curvature to adjust the amount of distraction provided through rotation. The first and second cam body 120, 122 may also have geometries that include smooth curves or generally planar sections that may facilitate stable positioning in final desired position. In on such embodiment illustrated in FIGS. 10-12, the first and second cam body 120, 122 each have a generally square profile and edges proximate the intersection of the sides are rounded.

It is possible for the first and second cam body 120, 122 to have a similar profile between opposite ends thereof. Alternatively, it is possible for at least a portion of the first and second cam body 120, 122 to have a different profile between opposite ends thereof. In certain embodiments, the first and second cam body 120, 122 have a convex profile between opposite ends thereof.

The first and second cam body 120, 122 may be fabricated of various materials using the concepts of the invention. Examples of these materials include biocompatible metals or metal alloys, biocompatible plastics, bio-absorbable materials, or actual human bone specially processed for use in orthopedic surgery, known as allograft.

The surface coating and/or texture on the first and second cam body 120, 122 may facilitate bone growth that engages with the surface of the first and second cam body 120, 122 to thereby reduce the potential of the first and second cam body 120, 122 moving with respect to the bones after implantation.

To facilitate rotation of the first and second cam body 120, 122 during the process of positioning the first and second cam body 120, 122 between two bones, the first and second cam body 120, 122 may include an engagement mechanism 124. The engagement mechanism 124 may be provided proximate at least one end of at least one of the first and second cam body 120, 122.

Figure 13:
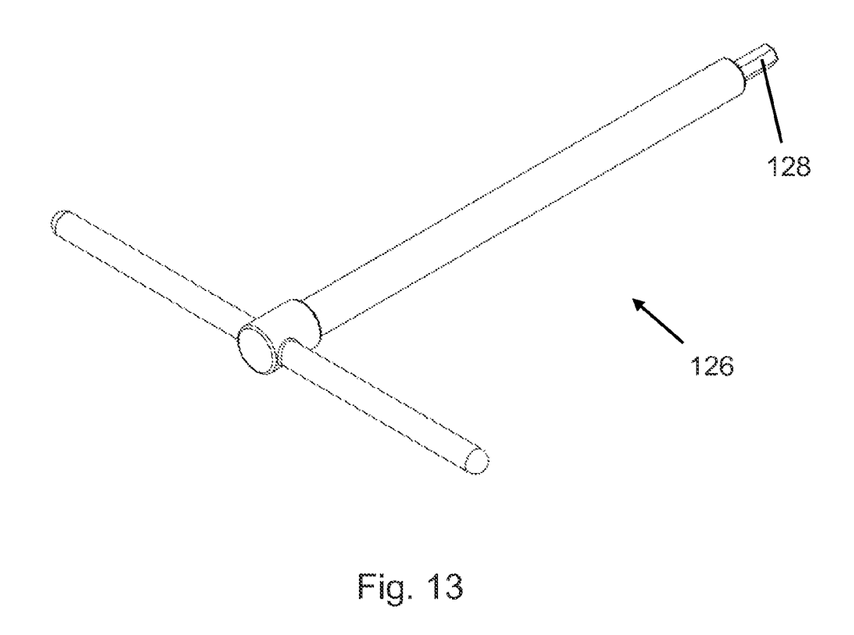
FIG. 13 is a perspective view of a tool for use with the orthopedic implant system.

The engagement mechanism 124 facilitates attachment of a driver 126 (FIG. 13) to the first and second cam body 120, 122. The driver 126 enhances the ability to accurately rotate the first and second cam body 120, 122. In certain embodiments, the driver 126 may be shaped similar to a conventional screw driver with a tip 128 that is shaped complementary to the engagement mechanism 124 such that at least a portion of the tip 128 may be inserted in the engagement mechanism 124. In other embodiments, the driver 126 may be shaped similar to a convention ratchet wrench to enable enhanced rotational force to be applied to the first and second cam body 120, 122.

In certain embodiments, the engagement mechanism 124 is a non-circular recess formed in at least one end of the first and second cam body 120, 122. Non-limiting examples of the shape of the engagement mechanism 124 recess include triangle, square, rectangle, pentagon, hexagon and star. The driver 126 may be formed with a shape and size that is similar to the shape and size of the non-circular engagement mechanism 124 so that rotation of the driver 126 causes the first and second cam body 120, 122 to which the driver 126 is attached to rotate.

In other embodiments, the engagement mechanism 124 is a non-circular extension (not shown) that extends from at least one end of the first cam body 120. Non-limiting examples of the shape of the engagement mechanism extension include triangle, square, rectangle, pentagon, hexagon and star. In this embodiment, the driver 126 may be formed with a recess having a shape and size that is similar to the shape and size of the non-circular extension so that rotation of the driver 126 causes the first and second cam body 120, 122 to which the driver 126 is attached to rotate.

Using multiple cam bodies 120, 122 in the orthopedic implant system facilitates greater flexibility in adjusting of the bones on opposite sides of the cam bodies. Using multiple cam bodies 120, 122 also facilitates disbursing the loads that are placed on the bones over a greater surface area to reduce the potential of such loads causing damage to the bones and/or the cam bodies.

A frame 140 is operably attached to at least one end of each cam body 120, 122. In certain embodiments, the cam bodies 120, 122 are mounted for rotation about an axis that is offset from a central axis of the cam body 120, 122. The frame 140 may include an end plate 142 from which at least one shaft 144 extends. The cam body 120, 122 has an aperture 146 formed therein that is adapted to receive one of the shafts 144. In certain embodiments, the shaft 144 has a size that is approximately the same as the size of the aperture 146.

The shafts 144 may be formed with a length that is greater than the length of the cam bodies 120, 122 so that the shafts 144 can extend through the cam bodies 120, 122 and into the lock plate 150, as described in more detail below.

While the shafts 144 are illustrated as being straight and having a generally cylindrical shape, it is possible for the shafts 144 to be formed with a variety of shapes. For example, at least a portion of the shafts 144 can be curved. Alternatively or additionally, at least a portion of the shafts 144 can be non-cylindrical such as having a triangular or square profile.

The end plate 142 may be formed with a height that is less than a height of the cam bodies 120, 122 so that contact between the end plate 142 and the bones on opposite sides of the cam bodies 120, 122 is avoided or minimized.

The aperture 146 may be offset from the center of the cam body 120, 122 so that rotation of the cam body 120, 122 with respect to the end plate 142 causes the cam body 120, 122 to shift laterally with respect to the end plate 142.

The frame 140 may also include a locking plate 150 that can engage an end of the cam body 120, 122 opposite the end plate 42 to thereby retain the cam body 120, 122 in a stationary position with respect to the end plate 142 as well as with respect to each other.

The locking plate 150 has a plurality of extensions 152 extending therefrom that are engage the cam body 120, 122 when the device is in the locked configuration (FIG. 3) and thereby prevent the cam body 120, 122 from rotating with respect to the locking plate 150. In certain embodiments, the extensions 152 have a non-circular profile such as square or hexagonal.

Figure 1:
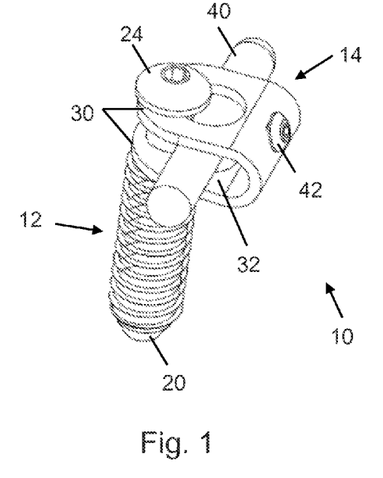
FIG. 1 is a perspective view of a pedicle screw system according to an embodiment of the invention where the pedicle screw system is in an assembled configuration.
Figure 2:
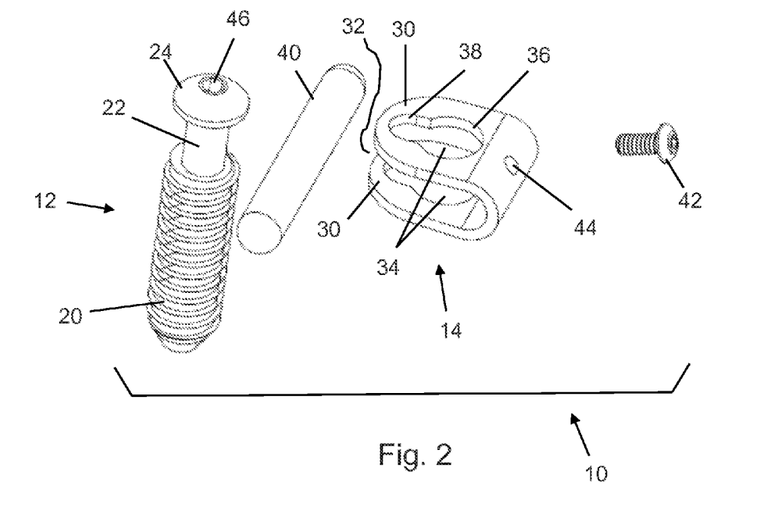
FIG. 2 is a perspective view of the pedicle screw system of FIG. 1 in an exploded configuration.
Figure 3:
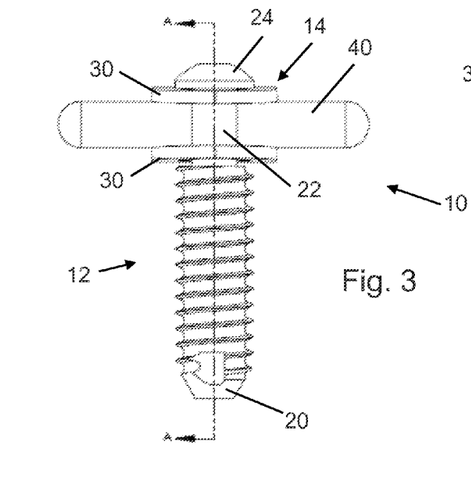
FIG. 3 is a side view of the pedicle screw system of FIG. 1.
Figure 4:
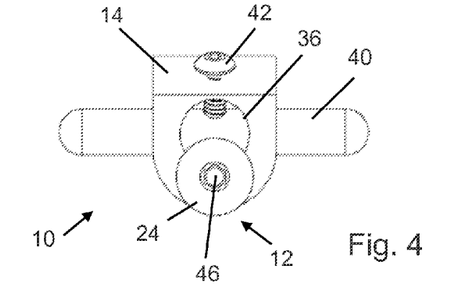
FIG. 4 is a top view of the pedicle screw system of FIG. 1
Figure 5:
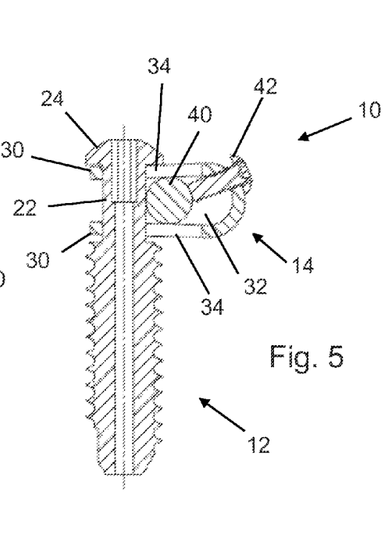
FIG. 5 is a sectional view of the pedicle screw system taken along a line A-A in FIG. 3.

The cam bodies 120, 122 have a recess 124 formed therein that is adapted to receive at least a portion of the extension 152. The recess 124 may have a shape that is similar to the shape of the extension 152. Using such a configuration prevents the cam body 120, 122 from rotating with respect to the locking plate 150 once at least a portion of the extension 152 is in the recess 124 as illustrated in FIG. 3. The locking plate 150 may also have apertures 156 formed therein through which the shafts 144 can extend there through.

The cam bodies 120, 122 may be formed with different lengths and/or the extensions 152 may be formed with different lengths. Using such a process enables one of the cam bodies 120, 122 to be retained in a desired position by moving one of the extensions 152 into one of the recesses 154. The other cam body 122 is then moved into a desired position before the locking plate 150 is moved into engagement with both of the cam bodies 120, 122.

In certain embodiments, the frame 140 may include more than two apertures 142. Such a configuration enables a spacing between the cam bodies 120, 122 to be changed depending on the location in which the orthopedic implant system is intended to be used.

In other embodiments, the cam bodies 120, 122 may be operably connected such that the cam bodies rotate in unison. An example of one technique that may be used to interconnect the cam bodies 120, 122 is gears (not shown) where the gears on each of the cam bodies 120, 122 engage each other. Forming the gears with the same diameter may cause the cam bodies 120, 122 to rotate at the same rate while forming the gears with different diameters may cause the cam bodies 120, 122 to rotate at different rates.

Figure 14:
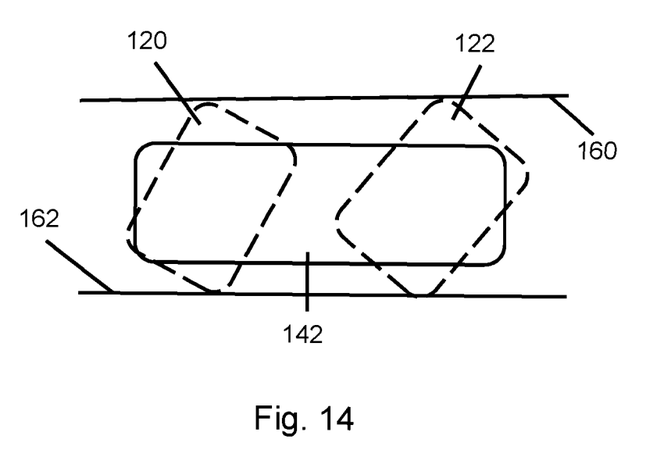
FIG. 14 is a sectional view of the first and second cam bodies engaging first and second bones.

The cam bodies 120, 122 may be manipulated by the surgeon by rotation where the cam configuration is utilized to contact and apply distracting force to the adjacent bone structures, such as vertebral bodies through opposite sides of the cam bodies 120, 122 contacting the first bone 160 and the second bone 162, as illustrated in FIG. 14. Once the desired positional relationship is established, the lock plate 150 may be used to retain the cam bodies 120, 122 in a substantially stationary position with respect to the frame 140, as illustrated in FIG. 12.

By adjusting cam bodies 120, 122 individually, the surgeon can achieve a desired orientation of the adjacent bone structures 160, 162 where the structures may be either parallel or non-parallel with respect to each other. Alternatively, the surgeon may utilize a temporary cam body that is comparable in general dimensions to a permanently implantable cam body.

This temporary cam body, also known as a trial device, may be employed so the surgeon can adjust the relative position of the adjacent structures to a desired position and then measure the distance between the structures. The surgeon can then replace the trial device with a permanent cam body that is of a size that will match the size determined during use of the trial.

The permanent device may include features, such as opposing flat surfaces, that, when rotated into place will re-establish the desired position of the adjacent structures with the flat surfaces placed against the structures surface creating a configuration that is more stable and resistant to loss of positioning.

After the implant is in the desired position, it is possible for the space between the bones that is not filled with the implant to be filled with a graft material. A person of skill in the art will appreciate that a variety of graft materials may be selected.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of changing a position of a first bone with respect to a second bone, wherein the method comprises:
providing an orthopedic implant system comprising a frame mechanism, a first cam body mounted with respect to the frame and a second cam body mounted with respect to the frame, wherein at least one of the first cam body and the second cam body has a non-circular profile;
inserting at least a portion of the orthopedic implant system between the first bone and the second bone;
rotating the first cam body with respect to the frame to move the first bone with respect to the second bone through contact of the first bone and the second bone by the first cam body; and
rotating the second cam body with respect to the frame to move the first bone with respect to the second bone through contact of the first bone and the second bone by the second cam body.

2. The method of claim 1, and further comprising preventing at least one of the first cam body and the second cam body from rotating with respect to the frame using a locking mechanism.

3. The method of claim 1, and further comprising placing a bone graft material between the first cam body and the second cam body to prevent at least one of the first cam body and the second cam body from rotating with respect to the frame.

4. The method of claim 1, wherein the first cam body is mounted for rotation about a first axis that extends between opposite ends thereof, wherein the second cam body is mounted for rotation about a second axis, wherein the first axis is parallel to the second axis and wherein the first axis is offset from a central axis of the first cam body.

5. The method of claim 1, wherein at least one of the first cam body and the second cam body comprises an engagement mechanism and wherein the method further comprises:
operably attaching a driver mechanism to the engagement mechanism; and
rotating the at least one of the first cam body and the second cam body using the driver mechanism.

6. The method of claim 1, wherein the at least one of the first cam body and the second cam body having the non-circular profile has an oval shape or has a generally planar surface along an edge thereof.

7. The method of claim 1, wherein the first cam body has a first length, wherein the second cam body has a second length and wherein the first length is different than the second length.

8. The method of claim 1, wherein rotating the first cam body and the second cam body with respect to the frame causes an orientation of the first bone to change with respect to the second bone.

9. The method of claim 1, wherein the at least one of the first cam body and the second cam body having the non-circular profile comprises a first non-circular surface portion and a second non-circular surface portion that are both positioned along an edge thereof.

10. The method of claim 9, wherein the first non-circular surface portion and the second non-circular surface portion are substantially linear.

11. The method of claim 9, wherein the first non-circular surface portion is at a position on the edge that is generally opposite the second non-circular surface portion.

12. The method of claim 1, wherein the first cam body and the second cam body each have a first end and a second end and wherein the frame mechanism is attached to the first cam body and the second cam body proximate the first and second ends thereof.

13. The method of claim 1, wherein the first cam body and the second cam body both have the non-circular profile.

* * * * *